United States Patent [19]

Werle et al.

[11] Patent Number: 4,730,084

[45] Date of Patent: Mar. 8, 1988

[54] PROCESS FOR THE PREPARATION OF DODECAMETHYLENEBISMELAMINE AND THE USE THEREOF

[75] Inventors: Peter Werle, Gelnhausen; Holger Focke, Bruchkoebel; Alwin Boes, Rodenbach, all of Fed. Rep. of Germany

[73] Assignee: Degussa Aktiengesellschaft, Frankfurt am Main, Fed. Rep. of Germany

[21] Appl. No.: 51,347

[22] Filed: May 19, 1987

Related U.S. Application Data

[62] Division of Ser. No. 833,693, Feb. 27, 1986, Pat. No. 4,683,307.

[30] Foreign Application Priority Data

Mar. 14, 1985 [DE] Fed. Rep. of Germany ....... 3509056

[51] Int. Cl.$^4$ .............................................. C07C 47/058
[52] U.S. Cl. ..................................................... 568/422

[58] Field of Search .......................................... 568/422

[56] References Cited

U.S. PATENT DOCUMENTS

| 4,389,333 | 6/1983 | Werle et al. | 568/422 |
| 4,683,307 | 8/1987 | Werle et al. | 568/422 |

FOREIGN PATENT DOCUMENTS 447670  4/1948  Canada ................................. 568/422

Primary Examiner—Werren B. Lone
Attorney, Agent, or Firm—Beveridge, DeGrandi & Weilacher

[57] ABSTRACT

The invention relates to a process for preparing dodecamethylenebismelamine (DMB) by reacting 2,4-diamino-6-chloro-1,3,5-triazine with 1,12-diaminododecane in an alkaline aqueous suspension, to which the diamine has been added in a water-miscible solvent. The product is used to stabilize aqueous formaldehye solutions.

2 Claims, No Drawings

PROCESS FOR THE PREPARATION OF DODECAMETHYLENEBISMELAMINE AND THE USE THEREOF

The present application is a divisional application of our copending application Ser. No. 833,693 filed Feb. 27, 1986 which is now U.S. Pat. No. 4,683,307, which is relied on herein.

The invention relates to the preparation of dodecamethylenebismelamine and the use thereof for stabilizing aqueous formaldehyde solutions.

Dodecamethylenebismelamine represented by the structural formula:

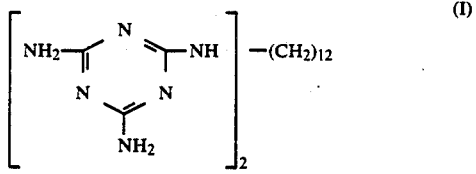

is used as a stabilizer for aqueous formaldehyde solutions and can be prepared according to the procedure described in EP-A2 79037 by reacting an aqueous suspension of 2,4-diamino-6-chloro-1,3,5-triazine with 1,12-diaminododecane in the presence of equivalent amounts of sodium hydroxide. This process yields a product with varying compositions and often with unsatisfactory properties in respect of the suitability of this product as a stabilizer.

In addition, if one attempts the synthesis of this product on an industrial scale, the desired bismelamne is generally obtained only as a mixture with the 1:1 adduct and other products and is thus unsuited for its intended purpose.

The preparation of solvates of bismelamine described in West German Patent Application 26 25 399 by reacting 2,4-diamino-6-chloro-s-triazine with diamine in dimethylformamide produces finely dispersed aqueous, DMF-containing suspensions from which the product can be separated only with great difficulty as a light-brown, probably dimethylformamide-containing preparation with a melting point of 110° C. In contrast, the melting point of pure bismelamine represented by formula (I), above, is 186°–188° C. In addition, the stabilizing effect on formaldehyde solutions is inadequate.

According to U.S. Pat. No. 2,544,071, decamethylenediamine can be prepared by reacting an aqueous suspension of 2,4-diamino-6-chloro-1,3,5-triazine with decamethylenediamine only as a crude product, the impurities of which necessitate an additional purification step.

The major purpose of the invention is to prepare a dodecamethylenebismelamine that is more suitable for stabilizing aqueous formaldehyde solutions.

The invention has as its object a process for the preparation of dodecamethylenebismelamine by reacting 2,4-diamino-6-chloro-1,3,5-triazine with 1,12-diaminododecane in an alkaline aqueous suspension and is characterized by adding to the suspension a sufficient amount of 1,12-diaminododecane dissolved in an organic, water-miscible solvent, more particularly an aliphatic alcohol, ketone, ether, or ether alcohol, carrying out the reaction at reflux temperature), cooling the formed reaction mixture down to room temperature (20°–25° C.) after the reaction has run its course, and separating the crystallized product, which precipitates in a readily filterable form. The addition of an aqueous, preferably 20 to 30%, sodium hydroxide solution ensures that the pH during the reaction does not exceed 10 and is preferably in the range of 8 to 10.

The reactants are used in a 1:1 molar ratio, if necessary with an excess of 5 up to 10% of 1,12-diaminododecane. Suitable alcohols have 1–3 carbon atoms; preferably, methanol, ethanol, n-propanol or isopropanol, or mixtures of these alcohols.

Other suitable solvents are, for example, dioxane, ethylene glycol monomethyl ether, acetone, methyl ethyl ketone and tetrahydrofuran.

The amount of organic solvent should be kept as small as possible. However, a sufficient amount should be added in each case, so that the diamine can be added to the reaction mixture in a totally dissolved state.

In carrying out the process, a 3 to 8 fold, preferably 4 to 6 fold, excess of the solvent, based on the weight of the diamine, is used.

The quantity ratio (parts by weight) of water to organic solvent in the reaction mixture is 3:1 to 10:1, preferably 5:1 to 7:1, whereas water and the triazine compound are present in the aqueous suspension in a ratio of 90:10 to 97:3, preferably 93:7 to 95:5.

According to the process of the present invention, aqueous suspensions that have been prepared by reacting cyanuric chloride with ammonia and sodium hydroxide after removal of the excess ammonia can also be used.

When selecting an appropriate organic solvent, it is also essential that the synthesized dodecamethylenebismelamine crystallize after the reaction mixture cools down to room temperature.

The process of the invention yields a product that exhibits an improved stabilizing effect in aqueous formaldehyde solutions without other purification steps that would otherwise be necessary.

This effect accomplished by the invention can be augmented by an additional positive effect, if the bismelamine is added not as a solid, but as a hemiformal-containing solution to the solutions to be stabilized.

As a result, stabilized formaldehyde solutions are obtained that foam a great deal less.

This advantageous effect can also be noted if dodecamethylenebismelamine is employed that has been prepared in accordance with teachings of prior art.

Unlike common organic solvents, dodecamethylenebismelamine is so readily soluble in methyl hemiformal at room temperature that one can easily prepare 20 to 25 weight percent solutions. This is connected to the additional advantage that impurities that may be present in the form of chlorine-containing triazine derivatives can be readily separated, since they are insoluble in methylhemiformal.

To prepare a hemiformal-containing stabilizer solution, paraformaldehyde is suspended in for example, methanol and, after adding an organic amine as catalyst, heated to boiling until a clear solution is obtained.

To the solution so obtained, there is added 15 to 25%, preferably 20 to 22, weight percent, based on the total amount, of dodecamethylenebismelamine; the mixture is stirred for another 20 to 30 minutes, any insoluble consistuents are filtered off, and a ready-to-use stabilizer solution is obtained after cooling. Preferably, methoxymethanol in the form of a methanolic solution containing 70 to 85 weight percent methoxy methanol is used as solvent.

Preferably, triethylamine, diethylamine, pyridine, and hexamethylenetetramine in an amount of 0.1 to 1.5 weight percent, based on the paraformaldehyde to be dissolved, are used as amines. Making the medium alkaline is essential for the action of the amines. They have no effect on the stabilization. Additions of dodecamethylenebismelamine in amounts of 0.001 to 0.05, preferably 0.005 to 0.015, weight percent, based on the total amount of the formaldehyde solution, are suitable for stabilization.

Stabilized formaldehyde solutions that foam much less are also obtained when dodecamethylenebismelamine, prepared in accordance with teachings of prior art and dissolved in methoxymethanol, is employed.

The use of methanol in the preparation of the hemiformal is of advantage, since the formaldehyde solution contins methanol anyway. In principle, however, other watersoluble alcohols can also be used.

PREPARATION OF DODECAMETHYLENEBISMELAMINE

Example 1

An aqueous suspension containing about 150 liters of water and 14.6 kg of 2,4-diamino-6-chloro-s-triazine is heated to 60° C.; a solution of 10 kg of 1,12-diaminododecane in 50 liters of n-propanol is then added and heated to reflux temperature while stirring. A pH range of 8–10 is maintained for about 2 hours by adding 20 weight percent sodium hydroxide solution. When the pH ceases to change, the mixture is stirred for another 1–2 hours, then cooled to about 20° C., and filtered. After washing with water and drying, a totally colorless product is obtained having a melting point of 186°–188° C. Yield: 19.2 kg (94% of theory).

The bismelamine was identified by IR and NMR spectroscopic analysis.

Example 2

The experiment is carried out as in Example 1, but 50 liters of ethanol is used as solvent for the diamine. There is obtained 19.4 (95% of theory) pure white bismelamine in the form of small granules.

Example 3

The experiment is carried out as in Example 1, but 45 liters of ethylene glycol monomethyl ether is used as solvent for the diamine. There is obtained 19.0 kg (93% of theory) of bismelamine.

STABLIZATION OF THE FORMALDEHYDE SOLUTIONS

Example 4

Formaldehyde solutions with a different formaldehyde content were analyzed; different amounts of the bismelamine prepared in accordance with the invention had been added to stabilize these solutions.

Results of experiments with bismelamine prepared in accordance with European Patent EP-A2-79037 and West German Patent Application DE-OS 26 25 399 are likewise apparent from Tables 1 and 2. To dissolve the stabilizers in the formaldehyde solutions, the latter were maintained at 80° C. for about 30 minutes while stirring. The amounts of stabilizer are given as weight percentages referred to the total formaldehyde solution. The shelf life is the amount of time during which the solution is stable. The end of shelf life is taken as that point in time when the first perceptible deposit of paraformaldehyde occurs.

TABLE 1

Aqueous solutions with 37 weight percent formaldehyde and 0.40 weight percent methanol

| Stabilizer (dodecamethylene-bismelamine) | Content (%) | Storage Temperature (°K.) | Shelf Life (d) |
|---|---|---|---|
| according to the invention | 0.005 | 273 | >60 |
|  | 0.01 | 273 | >120 |
| according to EP-A2-79037 | 0.005 | 273 | 6 |
|  | 0.01 | 273 | 28 |
| according to DE-OS 26 25 399 | 0.005 | 273 | 3 |
|  | 0.01 | 273 | 9 |

TABLE 2

Aqueous solutions with 50 weight percent formaldehyde and 0.60 weight percent methanol

| Stabilizer (dodecamethylene-bismelamine) | Content (%) | Storage Temperature (°K.) | Shelf Life (d) |
|---|---|---|---|
| according to the invention | 0.01 | 312 | >30 |
|  | 0.015 | 312 | >60 |
| according to EP-AS-79037 | 0.01 | 312 | 12 |
|  | 0.015 | 312 | 30 |
| according to DE-OS 26 25 399 | 0.01 | 312 | 1 |
|  | 0.02 | 312 | 8 |

PREPARATION OF HEMIFORMAL-CONTAINING STABILIZER SOLUTIONS

Example 5

40 kg of paraformaldehyde (90 weight percent) is suspended in 56 kg of methanol, and heated to boiling after addition of 0.5 kg of a catalyst in the form of an organic amine, such as triethylamine, diethylamine, pyridine, hexamethylenetetramine, etc. After about 20 minutes, a totally clear solution is obtained, to which 24.1 kg of DBM is added. The mixture is stirred for another 30 minutes and, if necessary, filtered off to remove insoluble minor constituents. After cooling, the 20 weight percent stablizer solution is ready for use.

Further variations and modifications of the invention will be apparent to those skilled in the art and are intended to be encompassed by the claims appended hereto.

The German Application P 35 09 056.1 filed Mar. 14, 1985 is relied on and incorporated herein.

We claim:

1. A process for the stabilization of aqueous formaldehyde solutions comprising introducing into said formaldehyde solutions a sufficient amount of dodecamethylenebismelamine in the form of a 15 to 25 weight percent solution, based on the total amount, wherein methoxymethanol (methyl hemiformal) is used as a solvent in form of a methanolic solution with a methoxymethanol content of 70–85%.

2. A process for the stabilization of aqueous formaldehyde solutions, comprising introducing a sufficient amount of dodecamethylenebismelamine into an aqueous formaldehyde solution wherein the bismelamine is a 15 to 25 weight percent solution, based on the total amount, and methoxymethanol (methyl hemiformal) is used as solvent in form of a methanolic solution with a methoxymethanol content of 70–85%, said dodecamethylenebismelamine having been prepared by a process comprising reacting 2,4-diamino-6-chloro-1,3,5-triazine with 1,12-diaminododecane as reactants in an alkaline, aqueous suspension, said 1,12-diaminododecane having been dissolved in a water-miscible, organic solvent and then added to said suspension, carrying out the reaction at reflux temperature, cooling the formed reaction mixture to room temperature and separating the resulting crystallized dodecamethylenebismelamine product.

* * * * *